United States Patent
Dumousseaux et al.

(10) Patent No.: US 9,114,076 B2
(45) Date of Patent: Aug. 25, 2015

(54) SOLID ANHYDROUS COSMETIC COMPOSITION

(75) Inventors: Christophe Dumousseaux, Antony (FR); Sylvie Gineston, St Maur des Fosses (FR)

(73) Assignee: L'OREAL, Paris (FR)

( * ) Notice: Subject to any disclaimer, the term of this patent is extended or adjusted under 35 U.S.C. 154(b) by 4 days.

(21) Appl. No.: 13/996,826

(22) PCT Filed: Dec. 21, 2011

(86) PCT No.: PCT/IB2011/055843
§ 371 (c)(1),
(2), (4) Date: Jul. 17, 2013

(87) PCT Pub. No.: WO2012/085855
PCT Pub. Date: Jun. 28, 2012

(65) Prior Publication Data
US 2013/0302394 A1    Nov. 14, 2013

Related U.S. Application Data

(60) Provisional application No. 61/437,386, filed on Jan. 28, 2011.

(30) Foreign Application Priority Data

Dec. 21, 2010 (FR) .................................. 10 60916

(51) Int. Cl.
| | | |
|---|---|---|
| *A61K 8/02* | (2006.01) | |
| *A61K 8/25* | (2006.01) | |
| *A61K 8/58* | (2006.01) | |
| *A61K 8/81* | (2006.01) | |
| *A61K 8/891* | (2006.01) | |
| *A61Q 1/02* | (2006.01) | |

(52) U.S. Cl.
CPC .................. *A61K 8/0279* (2013.01); *A61K 8/25* (2013.01); *A61K 8/585* (2013.01); *A61K 8/8111* (2013.01); *A61K 8/8117* (2013.01); *A61K 8/891* (2013.01); *A61Q 1/02* (2013.01); *A61K 2800/31* (2013.01)

(58) Field of Classification Search
CPC ............................ A61K 8/585; A61K 31/695
See application file for complete search history.

(56) References Cited

U.S. PATENT DOCUMENTS

| | | |
|---|---|---|
| 5,660,839 A | 8/1997 | Allec et al. |
| 5,939,083 A | 8/1999 | Allec et al. |
| 6,177,091 B1 | 1/2001 | Bara et al. |
| 2007/0009456 A1* | 1/2007 | Delacour et al. ................. 424/63 |
| 2007/0036736 A1 | 2/2007 | Kalla et al. |
| 2010/0197805 A1 | 8/2010 | Cassin |

FOREIGN PATENT DOCUMENTS

| | | |
|---|---|---|
| EP | 0 692 242 | 1/1996 |
| EP | 0 850 644 | 7/1998 |
| EP | 0 905 206 | 3/1999 |
| EP | 1 097 694 | 5/2001 |
| EP | 2 210 581 | 7/2010 |
| FR | 2 916 630 | 12/2008 |
| WO | 2007 017843 | 2/2007 |
| WO | 2008 012442 | 1/2008 |

OTHER PUBLICATIONS

Written Opinion Issued in French Application No. 1060916 Filed Dec. 21, 2010 (with English translation).
French Search Report Issued Aug. 30, 2011 in French Application Filed Dec. 21, 2010.
International Search Report Issued Jul. 3, 2012 in PCT/IB11/55843 Filed Dec. 21, 2011.

* cited by examiner

*Primary Examiner* — Alton Pryor
(74) *Attorney, Agent, or Firm* — Oblon, McClelland, Maier & Neustadt, L.L.P.

(57) ABSTRACT

The present invention relates especially to a solid anhydrous cosmetic composition comprising at least: at least 0.1% by weight of hollow particles relative to the total weight of the said composition, said composition being chosen from hydrophobic silica aerogel particles; a volatile oil; at least 5% by weight of at least one organopolysiloxane elastomer; and a wax.

16 Claims, No Drawings

SOLID ANHYDROUS COSMETIC COMPOSITION

The present invention relates to a solid anhydrous cosmetic composition.

A composition of the invention is especially a care and/or makeup composition intended to be applied to the skin and more particularly to facial skin.

Cosmetic compositions, especially foundations, are commonly used to give the skin an aesthetic colour, but also to hide imperfections of the skin relief such as wrinkles and/or fine lines. In this regard, many solid or fluid, anhydrous or non-anhydrous formulations have been developed to date to give the skin relief a smoothing effect.

There is currently a major trend in cosmetics towards developing anhydrous compositions. Specifically, the absence of water has the significant advantage of making it possible to dispense with the presence of the preserving agents usually required in order to prevent potential contamination, especially microbial or bacterial contamination, of water-based cosmetic formulations and thus to substantially reduce the risk of side reactions often associated with the presence of these preserving agents. What is more, by virtue of its anhydrous nature, such a composition also has the advantage of satisfying a consumer expectation in terms of cosmetic products that are "nomad" in the sense that they can be easily stored and transported under all conditions.

Similarly, solid textures are often preferred by users in comparison with liquid compositions. This solid texture is commonly obtained via the presence of waxes.

However, anhydrous solid cosmetic compositions, in particular foundations, incorporating such waxes are liable to give a greasy effect, which is generally little appreciated by users.

The present invention is specifically directed towards proposing anhydrous solid compositions that have good properties of masking imperfections or, in other words, of smoothing the skin relief, or even of remanence of these effects, and that moreover have no greasy effect.

Thus, according to one of its aspects, a subject of the invention is an anhydrous solid makeup and/or care cosmetic composition comprising at least:

at least 0.1% by weight of hollow particles relative to the total weight of the said composition;

a volatile oil;

at least 5% by weight of at least one organopolysiloxane elastomer; and a wax.

According to a particular variant, a subject of the invention is an anhydrous solid makeup and/or care cosmetic composition comprising at least:

at least 0.1% by weight of hollow particles relative to the total weight of the said composition, the said hollow particles being chosen from hydrophobic silica aerogel particles;

a volatile oil;

at least 5% by weight of at least one organopolysiloxane elastomer; and a wax.

For the purposes of the present invention, the term "anhydrous" refers to a composition comprising a content of less than or equal to 0.5% by weight of water relative to the total weight of the said composition. Where appropriate, such small amounts of water may especially be introduced by ingredients of the composition that may contain residual amounts thereof.

Preferably, an anhydrous composition according to the invention is totally free of water.

As emerges from the examples that follow, compositions in accordance with the invention prove to be advantageous in several respects.

First, the inventors have observed that the deposit formed makes it possible to obtain very good smoothing of the relief and good remanence of this effect over time.

In addition, a composition according to the invention proves to be easy for the user to take up, spreads easily on keratin material, in particular the skin, and is moreover entirely satisfactory in terms of cosmetic properties, comfort and moisturization.

By virtue of its anhydrous nature, such a composition also has the advantage of satisfying a consumer expectation in terms of cosmetic products that are "nomad" in the sense that they can be easily stored and transported under all conditions.

A composition of the invention may also comprise a physiologically acceptable medium.

The term "physiologically acceptable medium" is intended to denote a medium that is particularly suitable for applying a composition of the invention to keratin materials, especially the skin and more particularly to facial skin.

The physiologically acceptable medium is generally adapted to the nature of the support onto which the composition is to be applied, and also to the form in which the anhydrous composition is to be conditioned.

According to one advantageous embodiment variant, a solid anhydrous composition according to the invention may also comprise at least one hydrophobic film-forming polymer and/or one tackifying resin as described below.

According to another advantageous embodiment variant, a solid anhydrous composition according to the invention may also comprise, besides the abovementioned polymer particles, at least one particulate material as described below.

A subject of the present invention is also a cosmetic process for making up and/or caring for a keratin material, comprising at least the application to the said keratin material of a composition as defined previously.

A subject of the present invention is also a cosmetic process for masking skin relief imperfections, especially wrinkles and/or fine lines, comprising the application to the said keratin material of a composition as defined previously.

In this respect, and according to another of its subjects, the present invention relates to the use of a composition as defined previously for masking skin relief imperfections, and especially wrinkles and/or fine lines.

As emerges from the foregoing, the compositions under consideration according to the invention have a "solid" texture.

The term "solid" characterizes the state of the composition at room temperature (25° C.) and at atmospheric pressure (760 mmHg), i.e. a composition of sufficiently high consistency to conserve its form during storage.

Advantageously, a composition according to the invention may have a pasty texture.

This texture may especially be characterized by minimal strength, also known as the hardness, manifested by the compositions according to the invention when they are subjected to a test of penetration with a cylindrical spindle, this test clearly falling within the routine competence of a person skilled in the art.

For the purposes of the present invention, the term "hardness" is understood to mean the maximum penetration force obtained during the operation described below and expressed in grams.

It is measured at 20° C. using a texturometer sold under the name TAXT2i by the company RHEO, equipped with a cylindrical spindle, by measuring the change in force (compressive force or penetration force) (F) as a function of time.

A sample of the composition to be characterized is introduced into a crucible with a thickness at least equal to 20 mm and a surface area at least equal to 15 cm$^2$.

The sample is thermostatically maintained at 20° C. Nine measurements are taken for a same composition, either at different locations evenly distributed and spaced out over the sample, or on different samples for a same composition. The average of these nine measurements indicates the hardness of the composition with a 95% confidence interval.

Thus, advantageously, a composition according to the invention may have, at a temperature of 20° C., a hardness of greater than or equal to 100 g, or better still greater than or equal to 150 g, when it undergoes penetration, to a depth of 5 mm, of a cylindrical spindle 12.7 mm in diameter (P0.5R).

I—Hollow Particles

As emerges from the foregoing, a composition according to the invention comprises at least 0.1% by weight of hollow particles relative to the total weight of the said composition.

For the purposes of the invention, the term "particle" means a solid material that is insoluble in an aqueous phase or in a fatty phase and that has a mean size of between 0.5 and 50 microns and preferably between 1 and 30 microns.

Advantageously, a composition according to the invention comprises from 0.1% to 5% by weight, preferably from 0.1 to 1% by weight, and better still from 0.1% to 0.5% by weight of hollow particles relative to the total weight of the said composition.

As emerges from the text hereinbelow, the presence of hollow particles is particularly advantageous with regard to the objectives under consideration in the invention.

Specifically, with regard to their porous nature, these particles have liquid-absorbing capacity, which makes it possible especially to absorb a significant amount of oil(s) and thus to contribute firstly to the thickening of a composition according to the invention and thus to the acquisition of its solid structure, and secondly to the absence of a greasy effect felt by the user.

The oil-absorbing capacity of hollow particles in accordance with the invention is advantageously greater than 300 ml/100 g, preferably greater than 500 ml/100 g and better still greater than 1000 ml/100 g.

This capacity may especially be characterized by the "wet point" outlined in detail in the following chapter relating to hydrophobic silica aerogel particles.

Finally, besides these effects, the presence of the hollow particles quite probably contributes to the smoothing effect observed with a composition according to the invention and to the remanence over time of this effect.

In view of their small size, they can penetrate deep into the skin relief imperfections, for instance pores, and thus participate towards the levelling of the skin surface.

They also contribute towards scattering visible light, and give the composition a "soft focus" effect.

Finally, the presence of these hollow particles allows efficient absorption of sebum after application of the composition to the skin, and throughout the day.

The hollow particles that may be used according to the invention may be chosen especially from:
 hollow particles of an expanded polymer of vinylidene chloride and acrylonitrile or of vinylidene chloride, acrylonitrile and methyl methacrylate;
 hydrophobic silica aerogel particles; and
 mixtures thereof.

a) Hollow Particles of an Expanded Copolymer

The particles that may be used in the present invention may be hollow particles of an expanded polymer of vinylidene chloride and acrylonitrile or of vinylidene chloride, acrylonitrile and methyl methacrylate.

These polymers may be dry or hydrated.

Preferentially, the mass per unit volume of these particles is chosen in the range from 15 to 200 kg/m$^3$, preferably from 40 to 120 kg/m$^3$ and better still from 60 to 80 kg/m$^3$.

The particles that are suitable for use in the invention are, for example, microspheres of expanded terpolymer of vinylidene chloride, acrylonitrile and methyl methacrylate, sold under the brand name Expancel by the company Nobel Casco and in particular under the references 551 DE 12 (particle size D(0.5) of about 12 μm and mass per unit volume of about 40 kg/m$^3$), 551 DE 20 (particle size D(0.5) of about 15 to 25 μm and mass per unit volume of about 60 kg/m$^3$), 551 DE 50 (particle size D(0.5) of about 40 μm), 461 DE 50 and 642 WE 50 of about 50 μm of particle size D(0.5), 551 DE 80 (particle size D(0.5) of about 50 to 80 μm).

It is also possible to use particles of this same expanded terpolymer with a particle size D(0.5) of about 18 μm and a mass per unit volume of about 60 to 80 kg/m$^3$ (Expancel EL23) or with a particle size D(0.5) of about 34 μm and a mass per unit volume of about 20 kg/m$^3$.

Mention may also be made of the Expancel particles 551 DE 40 d42 (particle size D(0.5) of about 30 to 50 μm and a mass per unit volume of about 42 kg/m$^3$), 551 DE 80 d42 (particle size D(0.5) of about 50 to 80 μm and a mass per unit volume of about 42 kg/m$^3$), 461 DE 20 d70 (particle size D(0.5) of about 15 to 25 μm and a mass per unit volume of about 70 kg/m$^3$), 461 DE 40 d25 (particle size D(0.5) of about 35 to 55 μm and a mass per unit volume of about 25 kg/m$^3$), 461 DE 40 d60 (particle size D(0.5) of about 20 to 40 μm and a mass per unit volume of about 60 kg/m$^3$), 461 DET 40 d25 (particle size D(0.5) of about 35 to 55 μm and a mass per unit volume of about 25 kg/m$^3$), 051 DE 40 d60 (particle size D(0.5) of about 20 to 40 μm and a mass per unit volume of about 60 kg/m$^3$), 091 DE 40 d30 (particle size D(0.5) of about 35 to 55 μm and a mass per unit volume of about 30 kg/m$^3$), 091 DE 80 d30 (particle size D(0.5) of about 60 to 90 μm and a mass per unit volume of about 30 kg/m$^3$).

It is also possible to use particles of a polymer of vinylidene chloride and acrylonitrile or of vinylidene chloride, acrylonitrile and methyl methacrylate in unexpanded form, for instance those sold under the brand name Expancel with the reference 551 DU 10 (particle size D(0.5) of about 10 μm) or 461 DU 15 (particle size D(0.5) of about 15 μm).

b) Hydrophobic Silica Aerogel Particles

Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles that may be used in the present invention have a specific surface area per unit of mass ($S_M$) ranging from 500 to 1500 m$^2$/g, preferably from 600 to 1200 m$^2$/g and better still from 600 to 800 m$^2$/g, and a size expressed as the mean volume diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to one embodiment, the hydrophobic silica aerogel particles that may be used in the present invention have a size expressed as the mean volume diameter (D[0.5]) ranging from 1 to 30 μm, preferably from 5 to 25 μm, better still from 5 to 20 μm and even better still from 5 to 15 μm.

The specific surface area per unit of mass may be determined via the BET (Brunauer-Emmett-Teller) nitrogen absorption method described in the *Journal of the American Chemical Society*, vol. 60, page 309, February 1938 and corresponding to the international standard ISO 5794/1 (appendix D). The BET specific surface area corresponds to the total specific surface area of the particles under consideration.

The size of the hydrophobic silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

According to one advantageous embodiment, the hydrophobic silica aerogel particles used in the present invention have a specific surface area per unit of mass ($S_M$) ranging from 600 to 800 m$^2$/g and a size expressed as the mean volume diameter (D[0.5]) ranging from 5 to 20 μm and better still from 5 to 15 μm.

The hydrophobic silica aerogel particles used in the present invention may advantageously have a tamped density (ρ) ranging from 0.04 g/cm$^3$ to 0.10 g/cm$^3$ and preferably from 0.05 g/cm$^3$ to 0.08 g/cm$^3$.

In the context of the present invention, this density, known as the tamped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in cm$^3$ and m in g).

According to one embodiment, the hydrophobic silica aerogel particles that may be used in the present invention have a specific surface area per unit of volume $S_V$ ranging from 5 to 60 m$^2$/cm$^3$, preferably from 10 to 50 m$^2$/cm$^3$ and better still from 15 to 40 m$^2$/cm$^3$.

The specific surface area per unit of volume is given by the relationship: $S_V = S_M \cdot \rho$; where ρ is the tamped density expressed in g/cm$^3$ and $S_M$ is the specific surface area per unit of mass expressed in m$^2$/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The oil-absorbing capacity measured at the wet point, noted Wp, corresponds to the amount of water that needs to be added to 100 g of particle in order to obtain a homogeneous paste.

It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The hydrophobic silica aerogel particles are preferably of silylated silica type (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles that have been surface-modified by silylation, reference may be made to document U.S. Pat. No. 7,470,725.

Use will be made in particular of hydrophobic silica aerogel particles surface-modified with trimethylsilyl groups (trimethylsiloxyl silica).

As hydrophobic silica aerogel particles that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 m$^2$/g.

Mention may also be made of the aerogels sold by the company Cabot under the references Aerogel TLD 201, Aerogel OGD 201, Aerogel TLD 203, and ENOVA Aeorogel MT 1100.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 m$^2$/g (oil uptake equal to 1080 ml/100 g).

The hydrophobic silica aerogel particles that may be used in the present invention have a specific surface area per unit of mass ($S_M$) ranging from 500 to 1500 m$^2$/g, preferably from 600 to 1200 m$^2$/g and better still from 600 to 800 m$^2$/g, and a size expressed as the mean volume diameter (D[0.5]) ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

The use of the hollow particles according to the invention, in particular of hydrophobic silica aerogel particles, also advantageously makes it possible to improve the remanence of the cosmetic properties afforded by the composition on the skin, especially by limiting the impact of perspiration on the skin. The remanence properties over time of the colour, the matting effect and/or the homogeneity of the deposit on the skin may thus be improved.

II—Volatile Oil

The solid anhydrous composition according to the invention comprises, as fatty phase, at least one volatile oil, and especially at least one volatile oil as mentioned below.

Specifically, the presence of a volatile oil is advantageous insofar as it facilitates the dry application of the anhydrous composition.

According to the present invention, the term "oil" means a water-immiscible non-aqueous compound that is liquid at room temperature (25° C.) and at atmospheric pressure (760 mmHg).

An oily phase that is suitable for preparing an anhydrous cosmetic composition according to the invention may comprise hydrocarbon-based oils, silicone oils, fluoro oils or non-fluoro oils, or mixtures thereof.

The oils may be of animal, plant, mineral or synthetic origin. According to one embodiment variant, oils of plant origin are preferred.

The term "volatile oil" means any non-aqueous medium that is capable of evaporating on contact with the skin or the lips in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

To measure this evaporation rate, 15 g of oil or oil mixture to be tested are placed in a crystallizing dish 7 cm in diameter, placed on a balance that is in a large chamber of about 0.3 m$^3$ which is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

The volatile oils may be chosen from hydrocarbon-based oils containing from 8 to 16 carbon atoms, and especially $C_8$-$C_{16}$ branched alkanes (also known as isoparaffins), for instance isododecane (also known as 2,2,4,4,6-pentamethylheptane), isodecane and isohexadecane, for instance the oils sold under the trade names Isopar® or Permethyl®.

Volatile oils that may also be used include volatile silicones, for instance volatile linear or cyclic silicone oils, especially those with a viscosity ≤8 centistokes (cSt) ($8\times10^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 2 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

Preferably, a volatile oil in accordance with the invention is chosen from volatile silicones.

Advantageously, a composition of the invention may comprise from 10% to 60% by weight, preferably from 20% to 50% by weight and better still from 30% to 45% by weight of volatile oil(s) relative to the total weight of the said composition.

III—Organopolysiloxane Elastomer

The presence of an organopolysiloxane elastomer makes it possible to thicken the composition, to improve its application properties and to smooth out the skin relief.

Such a composition affords a very gentle feel and a matt effect after application, which is advantageous especially for application to the skin, in particular for foundation compositions. Such a compound is also advantageous in that it contributes towards filling the hollows present in keratin materials, and thus towards the smoothing properties manifested by a composition of the invention.

The term "organopolysiloxane elastomer" or "silicone elastomer" means a supple, deformable organopolysiloxane with viscoelastic properties and especially with the consistency of a sponge or a supple sphere. Its modulus of elasticity is such that this material withstands deformation and has limited stretchability and contractability. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolyzable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of a dimethylpolysiloxane with dimethylvinylsiloxy end groups and of methylhydrogenopolysiloxane with trimethylsiloxy end groups, in the presence of a platinum catalyst.

Compound (A) is the base compound for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from methylhydrogenopolysiloxanes containing trimethylsiloxy end groups, dimethylsiloxane-methylhydrogenosiloxane copolymers containing trimethylsiloxy end groups, and dimethylsiloxane-methylhydrogenosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located in any position of the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) may be chosen from methylvinylpolysiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

In particular, the organopolysiloxane elastomer may be obtained by reaction of a dimethylpolysiloxane containing dimethylvinylsiloxy end groups and of methylhydrogenopolysiloxane containing trimethylsiloxy end groups, in the presence of a platinum catalyst.

Advantageously, the sum of the number of ethylenic groups per molecule in compound (B) and of the number of hydrogen atoms bonded to silicon atoms per molecule in compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in an amount of from 0.1 to 1000 parts by weight and better still from 1 to 100 parts by weight, as clean platinum metal, per 1000 parts by weight of the total amount of compounds (A) and (B).

Advantageously, an organopolysiloxane elastomer in accordance with the invention is a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units. Thus, according to one particular mode of the invention, the composition comprises an organopolysiloxane elastomer free of polyoxyalkylene units and of polyglyceryl units.

The organopolysiloxane elastomer particles are conveyed in the form of a gel formed from an elastomeric organopolysiloxane included in at least one hydrocarbon-based oil and/or one silicone oil. In these gels, the organopolysiloxane particles are often non-spherical particles.

Non-emulsifying elastomers are especially described in patents EP 242 219, EP 285 886 and EP 765 656 and in patent application JP-A-61-194 009, the content of which is incorporated by way of reference.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

Spherical non-emulsifying elastomers that may be used include those sold under the names DC 9040, DC 9041, DC 9509, DC 9505 and DC 9506 by the company Dow Corning.

According to one particular mode, the composition of the invention comprises at least one non-emulsifying crosslinked silicone elastomer in the form of a gel in which the crosslinked silicone elastomer is dispersed in a silicone oil such as a dimethicone, in particular an elastomer having the INCI name: Dimethicone/vinyl dimethicone crosspolymer (and) dimethicone, such as the reference KSG-6 from the company Shin-Etsu.

According to another particular mode, a composition of the invention comprises at least one non-emulsifying crosslinked silicone elastomer in powder form, in particular an elastomer having the INCI name: Dimethicone/vinyl dimethicone crosspolymer, such as the reference DC9506 from Dow Corning.

Advantageously, an anhydrous composition of the invention may comprise from 5% to 50% by weight, preferably from 7% to 40% by weight and better still from 10% to 30% by weight of organopolysiloxane elastomer(s) relative to the total weight of the said composition.

In particular, the composition comprises from 5% to 50% by weight, preferably from 7% to 40% by weight and better still from 10% to 30% by weight of organopolysiloxane elastomer active material relative to the total weight of the said composition.

IV—Waxes

The wax under consideration in the context of the present invention is generally a lipophilic compound that is solid at room temperature (25° C.), with a solid/liquid reversible change of state, having a melting point of greater than or equal to 30° C., which may be up to 200° C. and in particular up to 120° C.

In particular, the waxes that are suitable for the invention may have a melting point of greater than or equal to 45° C. and in particular greater than or equal to 55° C.

The waxes that may be used in the compositions according to the invention are chosen from waxes that are solid at room temperature of animal, plant, mineral or synthetic origin, and mixtures thereof.

Thus, by virtue of the fluid nature of the wax at high temperature, it is easier to mix, manipulate and condition the composition according to the invention at such a temperature.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Among these, mention may be made especially of isomerized jojoba oil such as the trans-isomerized partially hydrogenated jojoba oil manufactured or sold by the company Desert Whale under the trade reference Iso-Jojoba-50®, hydrogenated sunflower oil, hydrogenated castor oil, hydrogenated coconut oil, hydrogenated lanolin oil, and the bis(1,1,1-trimethylolpropane)tetrastearate sold under the name Hest 2T-4S® by the company Heterene.

Mention may also be made of silicone waxes ($C_{30-45}$ alkyl dimethicone) and fluoro waxes.

The waxes obtained by hydrogenation of castor oil esterified with cetyl alcohol, sold under the names Phytowax ricin 16L64® and 22L73® by the company Sophim, may also be used. Such waxes are described in patent application FR-A-2 792 190.

A wax that may be used is a $C_{20}$-$C_{40}$ alkyl (hydroxystearyloxy)stearate (the alkyl group containing from 20 to 40 carbon atoms), alone or as a mixture.

Such a wax is especially sold under the names Kester Wax K 82 P®, Hydroxypolyester K 82 P® and Kester Wax K 80 P® by the company Koster Keunen.

Preferably, the composition according to the invention comprises at least one wax chosen from ester waxes, polyethylene waxes and microcrystalline waxes, and mixtures thereof, preferably at least one polyethylene wax.

Advantageously, a composition of the invention may comprise from 1% to 15% by weight and preferably from 2% to 10% by weight of wax(es) relative to the total weight of the said composition.

According to one preferred embodiment, a solid anhydrous composition in accordance with the invention comprises hollow particles at least partly formed from hydrophobic silica aerogel particles, at least one volatile silicone and preferably at least two volatile silicones, at least one non-emulsifying elastomer is organopolysiloxane elastomer, preferably a crosslinked polymer of dimethicone/vinyl dimethicone (and) dimethicone, and at least one wax chosen from polyethylene waxes.

V—Hydrophobic Film-Forming Polymer/Tackifying Resin

According to one advantageous embodiment variant, an anhydrous composition of the invention may also comprise at least one hydrophobic film-forming polymer and/or one tackifying resin.

The presence of such a compound is advantageous insofar as it makes it possible to improve, in synergy with the presence of the hollow particles and the volatile oil, the remanence of the smoothing effect on the skin relief manifested by a composition according to the invention.

Advantageously, a composition of the invention may comprise from 1% to 25% by weight and preferably from 2% to 15% by weight of hydrophobic film-forming the polymer(s) and/or tackifying resin(s) relative to the total weight of the said composition.

Hydrophobic Film-Forming Polymer

A hydrophobic film-forming polymer in accordance with the invention may be a polymer chosen from the group comprising: polyamide silicone block polymers, block ethylenic polymers, vinyl polymers comprising at least one carbosiloxane dendrimer derivative, copolymers comprising carboxylate groups and polydimethylsiloxane groups, and silicone resins, and mixtures thereof.

a) Silicone Resins

According to one embodiment variant, a composition according to the invention may comprise, as hydrophobic film-forming polymer, at least one silicone resin.

As silicone resins that may be used in the compositions according to the invention, use may be made, for example, of silicone resins of MQ type, of T type or of MQT type.

MQ Resins

As examples of silicone resins of MQ type, mention may be made of the alkyl siloxysilicates of formula $[(R1)_3SiO_{1/2}]_x$ $(SiO_{4/2})_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of trimethyl siloxysilicate type, mention may be made of those sold under the reference SR1000 by the company Momentive Performance Materials, under the reference TMS 803 by the company Wacker, or under the name KF-7312J by the company Shin-Etsu or DC 749 or DC 593 by the company Dow Corning.

As silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described especially in U.S. Pat. No. 5,817,302.

T Resins

Examples of silicone resins of type T that may be mentioned include the polysilsesquioxanes of formula $(RSiO_{3/2})_x$ (units T) in which x is greater than 100 and such that the group R is an alkyl group containing from 1 to 10 carbon atoms, said polysilsesquioxanes also possibly comprising Si—OH end groups.

Polymethylsilsesquioxane resins that may preferably be used are those in which R represents a methyl group, for instance those sold:

by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000 g/mol, or by the company Shin-Etsu under the reference KR220L, which are composed of units T of formula $CH_3SiO_{3/2}$ and have Si—OH (silanol) end groups, under the reference KR242A, which comprise 98% of units T and 2% of dimethyl units D and have Si—OH end groups, or alternatively under the reference KR251 comprising 88% of units T and 12% of dimethyl units D and have Si—OH end groups.

MQT Resins

Resins comprising MQT units that are especially known are those mentioned in document U.S. Pat. No. 5,110,890.

A preferred form of resin of MQT type are MQT-propyl (also known as MQTpr) resins. Such resins that may be used in the compositions according to the invention are especially the resins described and prepared in patent application WO 2005/075 542, the content of which is incorporated herein by reference.

Preferably, the silicone resin is chosen from the group comprising:

a) a resin of MQ type, chosen especially from (i) alkyl siloxysilicates, which may be trimethyl siloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, said polysilsesquioxanes also possibly comprising Si—OH end groups, and/or c) a resin of MQT type, especially of MQT-propyl type, which may comprise units (i) $(R1_3SiO_{1/2})_a$, (ii) $(R2_2SiO_{2/2})_b$, (iii) $(R3SiO_{3/2})_c$ and (iv) $(SiO_{4/2})_d$, with R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group, a being between 0.05 and 0.5,
b being between 0 and 0.3,
c being greater than zero,
d being between 0.05 and 0.6,
a+b+c+d=1, and a, b, c and d being mole fractions, on condition that more than 40 mol % of the groups R3 of the siloxane resin are propyl groups.

b) Block Ethylenic Copolymer

According to one embodiment of the invention, the hydrophobic film-forming polymer is a block ethylenic copolymer, containing at least a first block with a glass transition temperature (Tg) of greater than or equal to 40° C. and being totally or partly derived from one or more first monomers, which are such that the homopolymer prepared from these monomers has a glass transition temperature of greater than or equal to 40° C., and at least a second block with a glass transition temperature of less than or equal to 20° C. and being derived totally or partly from one or more second monomers, which are such that the homopolymer prepared from these monomers has a glass transition temperature of less than or equal to 20° C., the said first block and the said second block being connected together via a statistical intermediate segment comprising at least one of the said first constituent monomers of the first block and at least one of the said second constituent monomers of the second block, and the said block copolymer having a polydispersity index I of greater than 2.

The block polymer used according to the invention thus comprises at least one first block and at least one second block and is prepared exclusively from monofunctional monomers. This means that the block ethylenic polymer used according to the present invention does not contain any multifunctional monomers, which make it possible to break the linearity of a polymer so as to obtain a branched or even crosslinked polymer, as a function of the content of multifunctional monomer. The polymer used according to the invention does not, either, contain any macromonomers (the term "macromonomer" means a monofunctional monomer containing pendent groups of polymeric nature, and preferably having a molecular mass of greater than 500 g/mol, or alternatively a polymer comprising on only one of its ends a polymerizable (or ethylenically unsaturated) end group), which are used in the preparation of a grafted polymer.

The term "block" polymer means a polymer comprising at least two different blocks and preferably at least three different blocks.

The term "ethylenic" polymer means a polymer obtained by polymerization of ethylenically unsaturated monomers.

It is pointed out that, in the text hereinabove and hereinbelow, the terms "first" and "second" blocks do not in any way condition the order of the said blocks in the structure of the polymer.

The first block and the second block of the polymer used in the invention may be advantageously mutually incompatible.

The term "mutually incompatible blocks" means that the mixture formed from a polymer corresponding to the first block and from a polymer corresponding to the second block is not miscible in the polymerization solvent that is in major amount by weight for the block polymer, at room temperature (25° C.) and atmospheric pressure ($10^5$ Pa), for a content of the mixture of the said polymers of greater than or equal to 5% by weight, relative to the total weight of the mixture of the said polymers and of the said polymerization solvent, it being understood that:

i) the said polymers are present in the mixture in a content such that the respective weight ratio ranges from 10/90 to 90/10, and that ii) each of the polymers corresponding to the first and second blocks has an average (weight-average or number-average) molecular mass equal to that of the block polymer ±15%.

In the case of a mixture of polymerization solvents, and in the event that two or more solvents are present in identical mass proportions, the said polymer mixture is immiscible in at least one of them. Needless to say, in the case of a polymerization performed in a single solvent, this solvent is the solvent that is in major amount.

The block polymer according to the invention comprises at least a first block and at least a second block that are connected together via an intermediate segment comprising at least one constituent monomer of the first block and at least one constituent monomer of the second block. The intermediate segment (also known as the intermediate block) has a glass transition temperature Tg that is between the glass transition temperatures of the first and second blocks.

The intermediate segment is a block comprising at least one constituent monomer of the first block and at least one constituent monomer of the second block of the polymer allowing these blocks to be "compatibilized".

Advantageously, the intermediate segment comprising at least one constituent monomer of the first block and at least one constituent monomer of the second block of the block polymer is a statistical polymer.

Preferably, the intermediate block is derived essentially from constituent monomers of the first block and of the second block.

The term "essentially" means at least 85%, preferably at least 90%, better still 95% and even better still 100%.

The block polymer according to the invention is advantageously a film-forming block ethylenic polymer.

The term "film-forming polymer" means a polymer that is capable of forming, by itself or in the presence of an auxiliary film-forming agent, a continuous deposit on a support, especially on keratin materials.

Preferentially, the polymer according to the invention does not comprise any silicon atoms in its backbone. The term "backbone" means the main chain of the polymer, as opposed to the pendent side chains.

Preferably, the polymer according to the invention is not water-soluble, i.e. the polymer is not soluble in water or in a mixture of water and linear or branched lower monoalcohols containing from 2 to 5 carbon atoms, for instance ethanol, isopropanol or n-propanol, without modifying the pH, at the solids content of at least 1% by weight, at room temperature (25° C.).

Preferably, the polymer according to the invention is not an elastomer.

The polydispersity index of the polymer of the invention is greater than 2, for example ranging from 2 to 9. Preferably, it is greater than or equal to 2.5, for example ranging from 2.5 to 8, and better still greater than or equal to 2.8 and especially ranging from 2.8 to 6.

The polydispersity index I of the polymer is equal to the ratio of the weight-average molecular mass Mw to the number-average molecular mass Mn.

The weight-average molar mass (Mw) and number-average molar mass (Mn) are determined by gel permeation liquid chromatography (THF solvent, calibration curve established with linear polystyrene standards, refractometric detector).

The weight-average mass (Mw) of the polymer according to the invention is preferably less than or equal to 300 000; it ranges, for example, from 35 000 to 200 000 and better still from 45 000 to 150 000 g/mol.

The number-average mass (Mn) of the polymer according to the invention is preferably less than or equal to 70 000; it ranges, for example, from 10 000 to 60 000 and better still from 12 000 to 50 000 g/mol.

First Block with a Tg of Greater than or Equal to 40° C.

The block with a Tg of greater than or equal to 40° C. has, for example, a Tg ranging from 40 to 150° C., preferably greater than or equal to 50° C., for example ranging from 50° C. to 120° C. and better still greater than or equal to 60° C., for example ranging from 60° C. to 120° C.

The glass transition temperatures indicated for the first and second blocks may be theoretical Tg values determined from the theoretical Tg values of the constituent monomers of each of the blocks, which may be found in a reference manual such as the Polymer Handbook, 3rd Edition, 1989, John Wiley.

The block with a Tg of greater than or equal to 40° C. may be a homopolymer or a copolymer.

The block with a Tg of greater than or equal to 40° C. may be derived totally or partially from one or more monomers which are such that the homopolymer prepared from these monomers has a glass transition temperature of greater than or equal to 40° C. This block may also be referred to as a "rigid block".

When this block is a homopolymer, it is derived from only one type of monomer for which the Tg of the corresponding homopolymer is greater than or equal to 40° C.

In the case where the first block is a copolymer, it may be totally or partially derived from one or more monomers, the nature and concentration of which are chosen such that the Tg of the resulting copolymer is greater than or equal to 40° C. The copolymer may comprise, for example:

monomers which are such that the homopolymers prepared from these monomers have Tg values of greater than or equal to 40° C., for example a Tg ranging from 40° C. to 150° C., preferably greater than or equal to 50° C., for example ranging from 50° C. to 120° C. and better still greater than or equal to 60° C., for example ranging from 60° C. to 120° C., and monomers which are such that the homopolymers prepared from these monomers have Tg values of less than 40° C., chosen from monomers with a Tg of between 20° C. and 40° C. and/or monomers with a Tg of less than or equal to 20° C., for example a Tg ranging from −100° C. to 20° C., preferably less than 15° C., especially ranging from −80° C. to 15° C. and better still less than 10° C., for example ranging from −50° C. to 0° C., as described later. The monomers and the proportions thereof are preferably chosen such that the glass transition temperature of the first block is greater than or equal to 40° C.

The first monomers whose homopolymers have a glass transition temperature of greater than or equal to 40° C. are chosen, preferably, from the following monomers, also known as the main monomers:

the methacrylates of formula $CH_2=C(CH_3)-COOR_1$ in which $R_1$ represents a linear or branched unsubstituted alkyl group containing from 1 to 4 carbon atoms, such as a methyl, ethyl, propyl or isobutyl group or $R_1$ represents a $C_4$ to $C_{12}$ cycloalkyl group, preferably a $C_8$ to $C_{12}$ cycloalkyl, such as isobornyl methacrylate, the acrylates of formula $CH_2=CH-COOR_2$ in which $R_2$ represents a $C_4$ to $C_{12}$ cycloalkyl group such as an isobornyl group or a tert-butyl group, the (meth)acrylamides of formula:

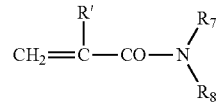

in which $R_7$ and $R_8$, which may be identical or different, each represent a hydrogen atom or a linear or branched $C_1$ to $C_{12}$ alkyl group such as an n-butyl, t-butyl, isopropyl, isohexyl, isooctyl or isononyl group; or $R_7$ represents H and $R_8$ represents a 1,1-dimethyl-3-oxobutyl group, and R' denotes H or methyl. Examples of monomers that may be mentioned include N-butylacrylamide, N-tert-butylacrylamide, N-isopropylacrylamide, N,N-dimethylacrylamide and N,N-dibutylacrylamide, and mixtures thereof.

According to one embodiment, the first block is obtained from:

i) at least one acrylate monomer of formula $CH_2=CH-COOR_2$ in which $R_2$ represents a $C_4$ to $C_{12}$ cycloalkyl group, preferably a $C_8$ to $C_{12}$ cycloalkyl, such as isobornyl, ii) and at least one methacrylate monomer of formula $CH_2=C(CH_3)-COOR'_2$ in which $R'_2$ represents a $C_4$ to $C_{12}$ cycloalkyl group, preferably a $C_8$ to $C_{12}$ cycloalkyl, such as isobornyl.

Preferably, $R_2$ and $R'_2$ represents, independently or simultaneously, an isobornyl group.

The first block may be obtained exclusively from the said acrylate monomer and from the said methacrylate monomer. Preferably, these monomers are in mass proportions of between 30/70 and 70/30, preferably between 40/60 and 60/40, especially about 50/50.

The proportion of the first block advantageously ranges from 20% to 90%, better still from 30% to 80% and even better still from 60% to 80% by weight of the polymer.

According to one embodiment, the first block is obtained by polymerization of isobornyl methacrylate and isobornyl acrylate.

Second Block with a Glass Transition Temperature of Less than 20° C.

The second block advantageously has a glass transition temperature Tg of less than or equal to 20° C., for example, a Tg ranging from −100° C. to 20° C., preferably less than or equal to 15° C., especially ranging from −80° C. to 15° C. and better still less than or equal to 10° C., for example ranging from −100° C. to 10° C., especially ranging from −30° C. to 10° C.

The second block is totally or partially derived from one or more second monomers, which are such that the homopolymer prepared from these monomers has a glass transition temperature of less than or equal to 20° C.

The monomer with a Tg of less than or equal to 20° C. (known as the second monomer) is preferably chosen from the following monomers:

the acrylates of formula $CH_2=CH-COOR_3$ $R_3$ representing a linear or branched $C_1$ to $C_{12}$ unsubstituted alkyl group, with the exception of the tert-butyl group, in which one or more heteroatoms chosen from O, N and S are optionally intercalated, the methacrylates of formula $CH_2=C(CH_3)-COOR_4$ $R_4$ representing a linear or branched $C_6$ to $C_{12}$ unsubstituted alkyl group, in which one or more heteroatoms chosen from O, N and S are optionally intercalated;

the vinyl esters of formula $R_5-CO-O-CH=CH_2$ in which $R_5$ represents a linear or branched $C_4$ to $C_{12}$ alkyl group;

ethers of vinyl alcohol and of a $C_4$ to $C_{12}$ alcohol,

N—($C_4$ to $C_{12}$)alkyl acrylamides, such as N-octylacrylamide, and mixtures thereof.

The preferred monomers with a Tg of less than or equal to 20° C. are isobutyl acrylate, 2-ethylhexyl acrylate or mixtures thereof in all proportions.

Each of the first and second blocks may contain in small proportion at least one constituent monomer of the other block.

Each of the first and/or second blocks may comprise, in addition to the monomers indicated above, one or more other monomers known as additional monomers, which are different from the main monomers mentioned above.

The nature and amount of this or these additional monomer(s) are chosen such that the block in which they are present has the desired glass transition temperature.

This additional monomer is chosen, for example, from (meth)acrylic acid, preferably acrylic acid, and mixtures thereof.

The additional monomer may represent 0.5% to 30% by weight relative to the weight of the polymer. According to one embodiment, the polymer of the invention does not contain any additional monomer.

According to one embodiment, the first block does not comprise any additional monomer.

According to a preferred embodiment, the second block comprises acrylic acid as additional monomer.

Preferably, the polymer of the invention comprises at least isobornyl acrylate and isobornyl methacrylate monomers in the first block and isobutyl acrylate and acrylic acid monomers in the second block.

Preferably, the polymer comprises at least isobornyl acrylate and isobornyl methacrylate monomers in equivalent weight proportion in the first block and isobutyl acrylate and acrylic acid monomers in the second block. Advantageously, the first block represents 70% by weight of the polymer.

Preferably, the acrylic acid represents 5% by weight of the polymer.

The block copolymer may advantageously comprise more than 2% by weight of acrylic acid monomers, and especially from 2% to 15% by weight, for example from 3% to 15% by weight, in particular from 4% to 15% by weight or even from 4% to 10% by weight of acrylic acid monomers, relative to the total weight of the said copolymer.

Preferably, the block copolymer comprises from 50% to 80% by weight of isobornyl methacrylate/acrylate, from 10% to 30% by weight of isobutyl acrylate and from 2% to 10% by weight of acrylic acid.

Intermediate Segment

The intermediate segment (also known as the intermediate block) connects the first block and the second block of the polymer used according to the present invention. The intermediate segment results from the polymerization:

i) of the first monomer(s), and optionally of the additional monomer(s), which remain available after their polymerization to a maximum degree of conversion of 90% to form the first block, ii) and of the second monomer(s), and optionally of the additional monomer(s), added to the reaction mixture.

The formation of the second block is initiated when the first monomers no longer react or are no longer incorporated into the polymer chain either because they are all consumed or because their reactivity no longer allows them to be.

Thus, the intermediate segment comprises the first available monomers, resulting from a degree of conversion of these first monomers of less than or equal to 90%, during the introduction of the second monomer(s) during the synthesis of the polymer.

The intermediate segment of the block polymer is a statistical polymer (which may also be referred to as a statistical block). This means that it comprises a statistical distribution of the first monomer(s) and of the second monomer(s) and also of the additional monomer(s) that may be present.

Thus, the intermediate segment is a statistical block, as are the first block and the second block if they are not homopolymers (i.e. if they are both formed from at least two different monomers).

Process for Preparing the Copolymer:

The block ethylenic copolymer according to the invention is prepared by free radical polymerization, according to the techniques that are well known for this type of polymerization. In particular, it may be prepared according to the process described in patent application FR 0 953 625, the content of which is incorporated herein by reference.

Preferably, the block ethylenic copolymer is present in the composition in an active material content ranging from 0.1% to 60%, better still from 0.5% to 50%, better still from 1% to 30% and even better still from 1% to 40% by weight relative to the total weight of the composition.

Distillation of the Synthesis Solvent

It is possible to perform a step of total or partial removal of the said volatile oil or solvent (conventionally isododecane). This is then performed in particular by distillation, optionally under vacuum, and optional addition of non-volatile hydrocarbon-based ester oil comprising at least 16 carbon atoms and having a molar mass of less than 650 g/mol, such as octyldodecyl neopentanoate (especially 2-octyldodecyl neopentanoate).

This step is performed at elevated temperature and optionally under vacuum to distil off a maximum amount of volatile synthesis solvent, and is known to those skilled in the art.

c) Polyamide Silicone Block Polymer

According to another embodiment variant, a composition according to the invention comprises, as hydrophobic film-forming polymer, at least one polyamide silicone block polymer, also known as a silicone polyamide.

The silicone polyamides are preferably solid at room temperature (25° C.) and atmospheric pressure (760 mmHg).

For the purposes of the invention, the term "polymer" means a compound containing at least two repeating units, preferably at least three repeating units and better still ten repeating units.

The silicone polyamides of the composition of the invention may be polymers of the polyorganosiloxane type, for instance those described in documents U.S. Pat. No. 5,874,069, U.S. Pat. No. 5,919,441, U.S. Pat. No. 6,051,216 and U.S. Pat. No. 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

According to one variant of the invention, a polymer may also be used comprising at least one unit of formula (III) or (IV):

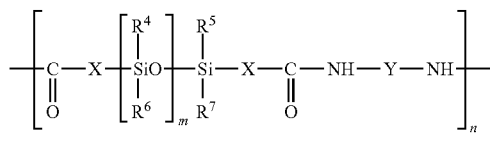

(III)

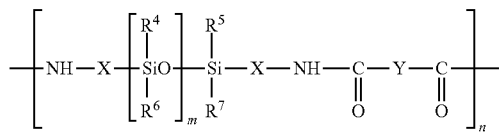

(IV)

in which:

1) $R^4$, $R^5$, $R^6$ and $R^7$, which may be identical or different, represent a group chosen from:

linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms, $C_6$-$C_{10}$ aryl groups, optionally substituted with one or more $C_1$-$C_4$ alkyl groups, polyorganosiloxane chains possibly containing one or more oxygen, sulfur and/or nitrogen atoms, 2) the groups X, which may be identical or different, represent a linear or branched $C_1$ to $C_{30}$ alkylenediyl group, possibly containing in its chain one or more oxygen and/or nitrogen atoms, 3) Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl, $C_1$ to $C_3$ hydroxyalkyl and $C_1$ to $C_6$ aminoalkyl groups, or 4) Y represents a group corresponding to the formula:

in which:

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^8$ represents a linear or branched $C_1$ to $C_{50}$ alkyl group or a polyorganosiloxane chain, possibly comprising one or more ester, amide, urethane, thiocarbamate, urea, thiourea and/or sulfonamide groups, which may possibly be linked to another chain of the polymer, and 5) n is an integer ranging from 2 to 500 and preferably from 2 to 200, and m is an integer ranging from 1 to 1000, preferably from 1 to 700 and better still from 6 to 200.

According to the invention, 80% of the groups $R^4$, $R^5$, $R^6$ and $R^7$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) branched $C_{30}$ to $C_{56}$ alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

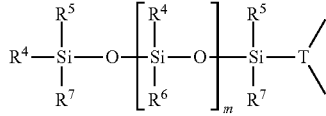

in which $R^4$, $R^5$, $R^6$, $R^7$, T and m are as defined above, and
h) polyorganosiloxane chains of formula:

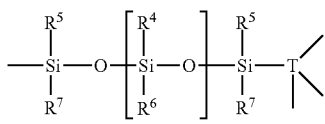

In these polyamides of formula (III) or (IV), m ranges from 1 to 700, in particular from 15 to 500 and especially from 50 to 200, and n ranges in particular from 1 to 500, preferably from 1 to 100 and better still from 4 to 25, X is preferably a linear or branched alkylene chain containing from 1 to 30 carbon atoms, in particular 1 to 20 carbon atoms, especially from 5 to 15 carbon atoms and more particularly 10 carbon atoms, and Y is preferably an alkylene chain that is linear or branched, or which may comprise rings and/or unsaturations, containing from 1 to 40 carbon atoms, in particular 1 to 20 carbon atoms and better still from 2 to 6 carbon atoms, in particular 6 carbon atoms.

In formulae (III) and (IV), the alkylene group representing X or Y can optionally contain in its alkylene part at least one of the following components:

1) one to five amide, urea, urethane or carbamate groups,
2) a $C_5$ or $C_6$ cycloalkyl group, and
3) a phenylene group optionally substituted with 1 to 3 identical or different $C_1$ to $C_3$ alkyl groups.

In formulae (III) and (IV), the alkylene groups may also be substituted with at least one component chosen from the group consisting of:
a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

In these formulae (III) and (IV), Y may also represent:

in which $R^8$ represents a polyorganosiloxane chain and T represents a group of formula:

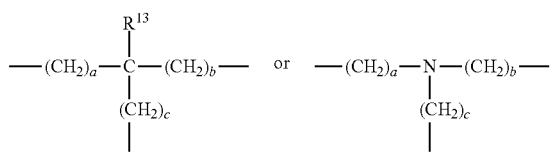

in which a, b and c are, independently, integers ranging from 1 to 10, and $R^{13}$ is a hydrogen atom or a group such as those defined for $R^4$, $R^5$, $R^6$ and $R^7$.

In formulae (III) and (IV), $R^4$, $R^5$, $R^6$ and $R^7$ preferably represent, independently, a linear or branched $C_1$ to $C_{40}$ alkyl group, preferably a $CH_3$, $C_2H_5$, $nC_3H_7$ or isopropyl group, a polyorganosiloxane chain or a phenyl group optionally substituted with one to three methyl or ethyl groups.

As has been seen previously, the polymer may comprise identical or different units of formula (III) or (IV).

Advantageously, the composition according to the invention comprises at least one polydimethylsiloxane block polymer of general formulae (III) and (IV) with an index m of about 15.

More preferably, the composition according to the invention comprises at least one polymer comprising at least one unit of formula (III) in which m ranges from 5 to 100, in particular from 10 to 75 and even more particularly is about 15; even more preferably, $R^4$, $R^5$, $R^6$ and $R^7$ independently represent a linear or branched $C_1$ to $C_{40}$ alkyl group, preferably a group $CH_3$, $C_2H_5$, $nC_3H_7$ or isopropyl in formula (III).

As examples of silicone polymers that may be used, mention may be made of one of the silicone polyamides obtained in accordance with Examples 1 to 3 of document U.S. Pat. No. 5,981,680.

According to one particularly preferred embodiment, the composition according to the invention comprises at least one polydimethylsiloxane block polymer of general formulae (III) and (IV) with an index m of about 100.

More preferably, the composition according to the invention comprises at least one polymer comprising at least one unit of formula (III) in which m ranges from 50 to 200, in particular from 75 to 150 and even more particularly is about 100; even more preferably, $R^4$, $R^5$, $R^6$ and $R^7$ independently represent a linear or branched $C_1$ to $C_{40}$ alkyl group, preferably a group $CH_3$, $C_2H_5$, $nC_3H_7$ or isopropyl in formula (III).

As examples of silicone polymers that may preferably be used according to this embodiment, mention may be made of the silicone polyamides sold by the company Dow Corning under the name DC 2-8179 (DP 100).

According to one preferred embodiment, the silicone polyamide comprises units of formula III, preferably in which the groups R4, R5, R6 and R7 represent methyl groups, one from among X and Y represents an alkylene group of 6 carbon atoms and the other represents an alkylene group of 11 carbon atoms, n representing the degree of polymerization, DP, of the polymer.

By way of example of such silicone polyamides, mention may be made of the compounds sold by the company Dow Corning under the names DC 2-8179 (DP 100) and DC 2-8178 (DP 15), the INCI name of which is Nylon-611/dimethicone copolymer.

d) Vinyl Polymer Comprising at Least One Carbosiloxane Dendrimer-Based Unit

According to one particular embodiment, a composition used according to the invention may comprise, as hydrophobic film-forming polymer, at least one vinyl polymer comprising at least one carbosiloxane dendrimer-based unit.

The vinyl polymer may especially have a backbone and at least one side chain, which comprises a carbosiloxane dendrimer structure.

The term "carbosiloxane dendrimer structure" in the context of the present invention represents a structure with branched groups of high molecular masses, the said structure having high regularity in the radial direction starting from the bond to the backbone. Such carbosiloxane dendrimer structures are described in the form of a highly branched siloxane-silylalkylene copolymer in the laid-open Japanese patent application Kokai 9-171 154.

According to one preferred mode, the vinyl polymer grafted with a carbosiloxane dendrimer used comprises at least one butyl acrylate monomer.

According to one embodiment, the vinyl polymer also comprises at least one fluoro organic group.

The vinyl polymers represented by the formulae presented below are preferable:
$CH_2=CHCOO-CH_2CH_2(CF_2)_6F.CH_2=CHCOO-CH_2CH_2(CF_2)_8F$.
$CH_2=CCH_3COO-CH_2CH_2(CF_2)_6F.CH_2=CCH_3COO-CH_2CH_2(CF_2)_8F$.
$CH_2=CHCOO-CH_2CF_3.CH_2=CCH_3COO-CH_2CF_3$ The vinyl polymers represented by the formulae presented below are particularly preferable:
$CH_2=CHCOO-CH_2CF_3.CH_2=CCH_3COO-CH_2CF_3$.

According to one preferred embodiment, vinyl polymers grafted within the meaning of the present invention are conveyed in an oil, which is preferably volatile, chosen from silicone oils and/or hydrocarbon-based oils.

According to one particular embodiment, the silicone oil may be cyclopentasiloxane.

According to another particular embodiment, a hydrocarbon-based oil may be isododecane.

Vinyl polymers grafted with at least one carbosiloxane dendrimer-based unit that may be particularly suitable for use in the present invention are the polymers sold under the names TIB 4-100, TIB 4-101, TIB 4-120, TIB 4-130, TIB 4-200, FA 4002 ID (TIB 4-202), TIB 4-220 and FA 4001 CM (TIB 4-230) by the company Dow Corning.

Preferably, the vinyl polymer grafted with at least one carbosiloxane dendrimer-based unit that may be used in a composition of the invention is an acrylate/polytrimethyl siloxymethacrylate copolymer, especially the product sold in isododecane under the name Dow Corning FA 4002 ID Silicone Acrylate by the company Dow Corning.

e) Copolymers Comprising Carboxylate Groups and Polydimethylsiloxane Groups

In the present patent application, the term "copolymer comprising carboxylate groups and polydimethylsiloxane groups" means a copolymer obtained from (a) one or more carboxylic (acid or ester) monomers, and (b) one or more polydimethylsiloxane (PDMS) chains.

In the present patent application, the term "carboxylic monomer" means both carboxylic acid monomers and carboxylic acid ester monomers. Thus, the monomer (a) may be chosen, for example, from acrylic acid, methacrylic acid, maleic acid, fumaric acid, itaconic acid, crotonic acid, esters thereof and mixtures of these monomers. Esters that may be mentioned include the following monomers: acrylate, methacrylate, maleate, fumarate, itaconate and/or crotonate. According to one preferred embodiment of the invention, the monomers in ester form are more particularly chosen from linear or branched, preferably $C_1$-$C_{24}$ and better still $C_1$-$C_{22}$ alkyl acrylates and methacrylates, the alkyl radical preferably being chosen from methyl, ethyl, stearyl, butyl and 2-ethylhexyl radicals, and mixtures thereof.

Thus, according to one particular embodiment of the invention, the copolymer comprises as carboxylate groups at least one group chosen from acrylic acid and methacrylic acid, and methyl, ethyl, stearyl, butyl or 2-ethylhexyl acrylate or methacrylate, and mixtures thereof.

In the present patent application, the term "polydimethylsiloxanes" (also known as organopolysiloxanes and abbreviated as PDMS) denotes, in accordance with what is generally accepted, any organosilicon polymer or oligomer of linear structure, of variable molecular weight, obtained by polymerization and/or polycondensation of suitably functionalized silanes, and consisting essentially of a repetition of main units in which the silicon atoms are linked together via oxygen atoms (siloxane bond $\equiv Si-O-Si\equiv$), comprising trimethyl radicals directly linked via a carbon atom to the said silicon atoms. The PDMS chains that may be used to obtain the copolymer used according to the invention comprise at least one polymerizable radical group, preferably located on at least one of the ends of the chain, i.e. the PDMS may contain, for example, a polymerizable radical group on the two ends of the chain or one polymerizable radical group on one end of the chain and one trimethylsilyl end group on the other end of the chain. The polymerizable radical group may especially be an acrylic or methacrylic group, in particular a group $CH_2=CR_1-CO-O-R_2$, in which $R_1$ represents a hydrogen or a methyl group and $R_2$ represents $-CH_2-$, $-(CH_2)_n-$ with n=3, 5, 8 or 10, $-CH_2-CH(CH_3)-CH_2-$, $-CH_2-CH_2-O-CH_2-CH_2-$, $-CH_2-CH_2-O-CH_2-CH_2-CH(CH_3)-CH_2-$, $-CH_2-CH_2-O-CH_2CH_2-O-CH_2-CH_2-CH_2-$.

The copolymers used in the composition of the invention are generally obtained according to the usual methods of polymerization and grafting, for example by free-radical polymerization (A) of a PDMS comprising at least one polymerizable radical group (for example on one of the ends of the chain or on both ends) and (B) of at least one carboxylic monomer, as described, for example, in documents U.S. Pat. No. 5,061,481 and U.S. Pat. No. 5,219,560.

The copolymers obtained generally have a molecular weight ranging from about 3000 to 200 000 and preferably from about 5000 to 100 000.

The copolymer used in the composition of the invention may be in its native form or in dispersed form in a solvent such as lower alcohols containing from 2 to 8 carbon atoms, for instance isopropyl alcohol, or oils, for instance volatile silicone oils (for example cyclopentasiloxane).

As copolymers that may be used in the composition of the invention, mention may be made, for example, of copolymers of acrylic acid and of stearyl acrylate containing polydimethylsiloxane grafts, copolymers of stearyl methacrylate containing polydimethylsiloxane grafts, copolymers of acrylic acid and of stearyl methacrylate containing polydimethylsiloxane grafts, copolymers of methyl methacrylate, butyl methacrylate, 2-ethylhexyl acrylate and stearyl methacrylate containing polydimethylsiloxane grafts. As copolymers that may be used in the composition of the invention, mention may be made in particular of the copolymers sold by the company Shin-Etsu under the names KP-561 (CTFA name: acrylates/dimethicone), KP-541 in which the copolymer is dispersed at 60% by weight in isopropyl alcohol (CTFA name: acrylates/dimethicone and isopropyl alcohol), and KP-545 in which the copolymer is dispersed at 30% in cyclopentasiloxane (CTFA name: acrylates/dimethicone and cyclopentasiloxane). According to one preferred embodiment of the invention, KP561 is preferably used; this copolymer is not dispersed in a solvent, but is in waxy form, its melting point being about 30° C.

Mention may also be made of the grafted copolymer of polyacrylic acid and dimethylpolysiloxane dissolved in isododecane, sold by the company Shin-Etsu under the name KP-550.

Tackifying Resin

The tackifying resin is in accordance with the invention generally has a number-average molecular weight of less than or equal to 10 000 g/mol, especially ranging from 250 to 10 000 g/mol, especially less than or equal to 5000 g/mol, especially ranging from 250 to 5000 g/mol, in particular less than or equal to 2000 g/mol, especially ranging from 250 to 2000 g/mol and better still less than or equal to 1000 g/mol and even more particularly ranging from 250 to 1000 g/mol.

The number-average molecular weights (Mn) are determined by gel permeation liquid chromatography (THF solvent, calibration curve established with linear polystyrene standards, refractometric detector).

This resin is advantageously a resin as described in the Handbook of Pressure Sensitive Adhesives, edited by Donatas Satas, 3rd edition, 1989, pp. 609-619.

It is advantageously chosen from colophony, colophony derivatives and hydrocarbon-based resins, and mixtures thereof.

Rosin is a mixture predominantly comprising organic acids known as rosin acids (mainly acids of abietic type and of pimaric type).

Three types of rosin exist: rosin ("gum rosin") obtained by incision on live trees, wood rosin, which is extracted from pine wood or stumps, and tall oil ("tall oil rosin"), which is obtained from a by-product originating from the production of paper.

The rosin derivatives may be derived in particular from the polymerization, hydrogenation and/or esterification (for example with polyhydric alcohols such as ethylene glycol, glycerol or pentaerythritol) of rosin acids. Examples that may be mentioned include the rosin esters sold under the reference Foral 85, Pentalyn H and Staybelite Ester 10 by the company Hercules; Sylvatac 95 and Zonester 85 by the company Arizona Chemical, or Unirez 3013 by the company Union Camp.

The hydrocarbon-based resins are chosen from indene hydrocarbon-based resins, aliphatic pentanediene resins, mixed resins of pentanediene and of indene, diene resins of cyclopentanediene dimers and diene resins of isoprene dimers, and mixtures thereof.

The hydrocarbon-based resins are chosen from low molecular weight polymers that may be classified, according to the type of monomer they comprise, as:

indene hydrocarbon-based resins, preferably such as resins derived from the polymerization in major proportion of indene monomer and in minor proportion of monomers chosen from styrene, methylindene and methylstyrene, and mixtures thereof. These resins may optionally be hydrogenated. These resins may have a molecular weight ranging from 290 to 1150 g/mol.

Examples of indene resins that may be mentioned include those sold under the reference Escorez 7105 by the company Exxon Chem., Nevchem 100 and Nevex 100 by the company Neville Chem., Norsolene 5105 by the company Sartomer, Picco 6100 by the company Hercules and Resinall by the company Resinall Corp., or the hydrogenated indene/methylstyrene/styrene copolymers sold under the name "Regalite" by the company Eastman Chemical, in particular Regalite R1100, Regalite R1090, Regalite R7100, Regalite R1010 Hydrocarbon Resin and Regalite R1125 Hydrocarbon Resin;

aliphatic pentanediene resins such as those derived from the majority polymerization of the 1,3-pentanediene (trans- or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500 g/mol.

Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear;

mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear;

diene resins of cyclopentanediene dimers such as those derived from the polymerization of first monomers chosen from indene and styrene, and of second monomers chosen from cyclopentanediene dimers such as dicyclopentadiene, methyldicyclopentanediene and other pentanediene dimers, and mixtures thereof. These resins generally have a molecular weight ranging from 500 to 800 g/mol, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.;

diene resins of isoprene dimers such as terpenic resins derived from the polymerization of at least one monomer chosen from α-pinene, β-pinene and limonene, and mixtures thereof. These resins can have a molecular weight ranging from 300 to 2000 g/mol. Such resins are sold, for example, under the names Piccolyte A115 and 5125 by Hercules or Zonarez 7100 or Zonatac 105 Lite by Arizona Chem.

Mention may also be made of certain modified resins such as hydrogenated resins, for instance those sold under the name Eastotac $C_6$-$C_{20}$ Polyolefin by the company Eastman Chemical Co., under the reference Escorez 5300 by the company Exxon Chemicals, or the resins Nevillac Hard or Nevroz sold by the company Neville Chem., the resins Piccofyn A-100, Piccotex 100 or Piccovar AP25 sold by the company Hercules or the resin SP-553 sold by the company Schenectady Chemical Co.

According to one preferred embodiment, the resin is chosen from indene hydrocarbon-based resins, in particular the hydrogenated indene/methylstyrene/styrene copolymers sold under the name "Regalite" by the company Eastman Chemical, such as Regalite R1100, Regalite R1090, Regalite R7100, Regalite R1010 Hydrocarbon Resin and Regalite R1125 Hydrocarbon Resin.

According to one preferred embodiment, a solid anhydrous composition in accordance with the invention comprises hollow particles at least partly formed from hydrophobic silica aerogels particles, at least one volatile silicone, at least one non-emulsifying elastomer as organopolysiloxane elastomer, preferably a crosslinked polymer of dimethicone/vinyl dimethicone (and) dimethicone, at least one wax, preferably chosen from polyethylene waxes, and at least one silicone resin of MQ type, in particular of trimethyl siloxysilicate type.

VI—Other Compounds

Non-Volatile Oil

According to another advantageous embodiment variant, a composition of the invention may comprise, besides the volatile oil described previously, at least one non-volatile oil.

The term "non-volatile oil" means an oil that remains on the skin or the keratin fibre at room temperature and atmospheric pressure. More specifically, a non-volatile oil has an evaporation rate strictly less than 0.01 mg/cm$^2$/min.

The non-volatile oils may be chosen especially from non-volatile hydrocarbon-based, fluoro and/or silicone oils.

Non-volatile hydrocarbon-based oils that may especially be mentioned include:

hydrocarbon-based oils of animal origin, hydrocarbon-based oils of plant origin, such as phytostearyl esters, such as phytostearyl oleate, phytostearyl isostearate and lauroyl/octyldodecyl/phytostearyl glutamate (Ajinomoto, Eldew PS203), triglycerides formed from fatty acid esters of glycerol, in particular in which the fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, millet oil, barley oil, rye oil, candlenut oil, passionflower oil, shea butter, aloe vera oil, sweet almond oil, peach stone oil, groundnut oil, argan oil, avocado oil, baobab oil, borage oil, broccoli oil, calendula oil, camellina oil, canola oil, carrot oil, safflower oil, flax oil, rapeseed oil, cotton oil, coconut oil, marrow seed oil, wheatgerm oil, jojoba oil, lily oil, macadamia oil, corn oil, meadowfoam oil, St John's Wort oil, monoi oil, hazelnut oil, apricot kernel oil, walnut oil, olive oil, evening primrose oil, palm oil, blackcurrant pip oil, kiwi seed oil, grapeseed oil, pistachio oil, winter squash oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stearineries Dubois or those sold under the names Miglyol 810®, 812® and 818® by the company Dynamit Nobel, linear or branched hydrocarbons, of mineral or synthetic origin, such as liquid paraffins and derivatives thereof, petroleum jelly, polydecenes, polybutenes, hydrogenated polyisobutene such as Parleam, and squalane, synthetic ethers containing from 10 to 40 carbon atoms, such as dicaprylyl ether, synthetic esters, for instance oils of formula $R_1COOR_2$, in which $R_1$ represents a linear or branched fatty acid residue containing from 1 to 40 carbon atoms, and $R_2$ represents a hydrocarbon-based chain that is especially branched, containing from 1 to 40 carbon atoms provided that $R_1+R_2 \geq 10$. The esters may be chosen especially from esters of alcohol and of fatty acid, for instance cetostearyl octanoate, esters of isopropyl alcohol, such as isopropyl myristate, isopropyl palmitate, ethyl palmitate, 2-ethylhexyl palmitate, isopropyl stearate, octyl stearate, hydroxylated esters, for instance isostearyl lactate, octyl hydroxystearate, alcohol or polyalcohol ricinoleates, hexyl laurate, neopentanoic acid esters, for instance isodecyl neopentanoate, isotridecyl neopentanoate, and isononanoic acid esters, for instance isononyl isononanoate and isotridecyl isononanoate, polyol esters and pentaerythritol esters, for instance dipentaerythrityl tetrahydroxystearate/tetraisostearate, esters of diol dimers and of diacid dimers, such as Lusplan DD-DA5® and Lusplan DD-DA7® sold by the company Nippon Fine Chemical and described in patent application US 2004-175 338, copolymers of a diol dimer and of a diacid dimer and esters thereof, such as dilinoleyl diol dimer/dilinoleic dimer copolymers and esters thereof, for instance Plandool-G, copolymers of polyols and of diacid dimers, and esters thereof, such as Hailuscent ISDA or the dilinoleic acid/butanediol copolymer, fatty alcohols that are liquid at room temperature, with a branched and/or unsaturated carbon-based chain containing from 12 to 26 carbon atoms, for instance 2-octyldodecanol, isostearyl alcohol and oleyl alcohol, $C_{12}$-$C_{22}$ higher fatty acids, such as oleic acid, linoleic acid or linolenic acid, and mixtures thereof, dialkyl carbonates, the two alkyl chains possibly being identical or different, such as dicaprylyl carbonate sold under the name Cetiol CC® by Cognis, oils of high molar mass, in particular with a molar mass ranging from about 400 to about 2000 g/mol and in particular from about 650 to about 1600 g/mol. As oils of high molar mass that may be used in the present invention, mention may be made especially of linear fatty acid esters with a total carbon number ranging from 35 to 70, for instance pentaerythrityl tetrapelargonate, hydroxylated esters, such as polyglyceryl-2 triisostearate, aromatic esters, such as tridecyl trimellitate, esters of branched $C_{24}$-$C_{28}$ fatty alcohols or fatty acids, such as those described in U.S. Pat. No. 6,491,927, and pentaerythritol esters, and especially triisoarachidyl citrate, glyceryl triisostearate, glyceryl tris(2-decyl)tetradecanoate, polyglyceryl-2 tetraisostearate or pentaerythrityl tetrakis(2-decyl)tetradecanoate; phenyl silicones, such as Belsil PDM 1000 from the company Wacker (MM=9000 g/mol), non-volatile polydimethylsiloxanes (PDMS), PDMSs comprising alkyl or alkoxy groups that are pendent and/or at the end of the silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, dimethicones or phenyl trimethicones with a viscosity of less than or equal to 100 cSt, and mixtures thereof; and also mixtures of these various oils, and mixtures thereof.

According to one preferred embodiment, the composition according to the invention comprises at least one non-volatile oil chosen from non-volatile silicone oils.

Advantageously, a composition of the invention comprises from 1% to 20% by weight and preferably from 2% to 10% by weight of non-volatile oil(s) relative to the total weight of the said composition.

According to another advantageous embodiment variant, a composition according to the invention may comprise, besides the abovementioned hollow polymer particles, at least one particulate material chosen from fillers; pigments; nacres; particles with a metallic tint; and mixtures thereof.

These compounds as a whole define the pulverulent phase of a composition according to the invention.

Pulverulent Phase

Advantageously, an anhydrous composition according to the invention comprises from 1% to 25% by weight, preferably from 5% to 20% by weight and better still from 10% to 20% by weight of pulverulent phase relative to the total weight of the said composition.

For the purposes of the invention, the term "fillers" should be understood as meaning colourless or white solid particles of any form, which are in an insoluble and dispersed form in the medium of the composition, irrespective of the temperature at which the composition is manufactured.

These fillers, of mineral or organic, natural or synthetic nature, give the composition containing them softness and give the makeup result a matt effect and uniformity.

Among the mineral fillers that may be used in the compositions according to the invention, mention may be made of natural or synthetic mica, talc, natural or synthetic sericite, silica, hydroxyapatite, boron nitride, calcium carbonate, hollow silica microspheres (Silica beads from Maprecos), glass or ceramic microcapsules; composites of silica and titanium dioxide, such as the TSG series sold by Nippon Sheet Glass or the Sunsil series marketed by the company Sunjin, and mixtures thereof.

Among the organic fillers that may be used in the compositions according to the invention, mention may be made of polyamide powders (Nylon® Orgasol from Atochem), poly-β-alanine powder and polyethylene powder, polytetrafluoroethylene (Teflon®) powder, lauroyllysine, tetrafluoroethylene polymer powders, spherical powders of crosslinked elastomeric organopolysiloxane, described especially in document JP-A-02-243612, such as those sold under the name Trefil Powder E-506C or DC9506 or DC9701 by the company Dow Corning, silicone resins, which are products of hydrolysis and polycondensation of siloxane mixtures of formulae $(R)_3SiOHCH_3$ and $Si(OCH_3)_4$, R representing an alkyl group containing from 1 to 6 carbon atoms (for example KSP100 from Shin-Etsu), silicone resin microbeads (for example Tospearl® from Toshiba), Polypore® L200 (Chemdal Corporation), polyurethane powders, in particular crosslinked polyurethane powders comprising a copolymer, the said copolymer comprising trimethylol hexyl lactone, for instance the polymer of hexamethylene diisocyanate/trimethylol hexyl lactone, sold under the name Plastic powder D-400® or Plastic Powder D-800® by the company Toshiki, and mixtures thereof.

Among the other organic fillers that may be used in the compositions according to the invention, mention may be made of starch-based or cellulose-based powders. Examples of such fillers that may be mentioned include the Dry Flo products sold by Akzo Nobel and the Cellubeads products sold by the company Daito Kasei.

According to one particular mode, the composition of the invention comprises at least one mineral filler chosen from composites of silica and of titanium dioxide.

Advantageously, the fillers in accordance with the invention are mineral fillers, preferably chosen from composites of silica and of titanium dioxide, mixed with spherical powders of crosslinked elastomeric organopolysiloxane. Such starting materials make it possible to improve the optical smoothing effect.

A composition according to the invention may also include particulate materials for colouring purposes.

They may especially be pigments, nacres and/or particles with metallic tint products, these materials possibly being surface-treated.

The term "pigments" should be understood as meaning white or coloured, mineral or organic particles that are insoluble in an aqueous solution, which are intended to colour and/or opacify the composition containing them.

The pigments may be white or coloured, and mineral and/or organic.

As mineral pigments that may be used in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Advantageously, the pigments in accordance with the invention are iron oxides and/or titanium dioxides.

The term "nacres" should be understood as meaning iridescent particles of any shape, especially produced by certain molluscs in their shell, or else synthesized.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres, sold by the company Eckart, and the Sunshine synthetic mica-based nacres, sold by the company Sun Chemical.

The nacres may more particularly have a yellow, pink, red, bronze, orange, brown, gold and/or coppery colour or tint.

As illustrations of nacres that may be used in the context of the present invention, mention may be made of gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nuantique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red-tinted nacres with a golden tint sold especially by the company Engelhard under the name Sunstone G012 (Gemtone); the pink nacres sold especially by the company Engelhard under the name Tan opale G005 (Gemtone); the black nacres with a golden tint sold especially by the company Engelhard under the name Nu antique bronze 240 AB (Timica); the blue nacres sold especially by the company Merck under the name Matte blue (17433) (Microna); the white nacres with a silvery tint sold especially by the company Merck under the name Xirona Silver; and the golden-green pinkish-orange nacres sold especially by the company Merck under the name Indian summer (Xirona), and mixtures thereof.

Advantageously, the nacres in accordance with the invention are micas coated with titanium dioxide or with iron oxide, and also bismuth oxychloride.

The term "particles with a metallic tint", within the meaning of the present invention, denotes particles whose nature, size, structure and surface state allow them to reflect the incident light, especially in a non-iridescent manner.

Particles with a substantially flat outer surface are also suitable, since they can, if their size, structure and surface state allow it, more easily give rise to a strong specular reflection, which may then be termed a mirror effect.

The particles with a metallic tint that may be used in the invention may, for example, reflect light in all the components of the visible region without significantly absorbing one or more wavelengths. The spectral reflectance of these particles may, for example, be greater than 70% and better still at least 80%, or even 90% or 95%, in the range 400-700 nm.

These particles generally have a thickness of less than or equal to 1 µm, especially less than or equal to 0.7 µm and in particular less than or equal to 0.5 µm.

The particles with a metallic tint that may be used in the invention are in particular chosen from:
- particles of at least one metal and/or of at least one metal derivative,
- particles comprising a monomaterial or multimaterial organic or mineral substrate, at least partially coated with at least one layer with a metallic tint comprising at least one metal and/or at least one metal derivative, and mixtures of said particles.

Among the metals that may be present in said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" is intended to denote compounds derived from metals, especially oxides, fluorides, chlorides and sulfides.

Among the metal derivatives that may be present in said particles, mention may be made especially of metal oxides, for instance titanium oxide, especially $TiO_2$, iron oxide, especially $Fe_2O_3$, tin oxide, chromium oxide, barium sulfate and the following compounds: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

Illustrations of these particles that may be mentioned include aluminium particles, such as those sold under the names Starbrite 1200 EAC® by the company Siberline and Metalure® by the company Eckart.

Mention may also be made of metal powders of copper or of alloy mixtures such as the references 2844 sold by the company Radium Bronze, metallic pigments, for instance aluminium or bronze, such as those sold under the names Rotosafe 700 from the company Eckart, silica-coated aluminium particles sold under the name Visionaire Bright Silver from the company Eckart, and metal alloy particles, for instance the silica-coated bronze (alloy of copper and zinc) powders sold under the name Visionaire Bright Natural Gold from the company Eckart.

As illustrations of particles of this second type, mention may be made more particularly of:

Glass particles coated with a metallic layer, especially those described in documents JP-A-09188830, JP-A-10158450, JP-A-10158541, JP-A-07258460 and JP-A-05017710.

As illustrations of these particles comprising a glass substrate, mention may be made of those coated, respectively, with silver, gold or titanium, in the form of platelets, sold by the company Nippon Sheet Glass under the name Microglass Metashine. Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company. Those coated either with brown iron oxide or with titanium oxide, tin oxide or a mixture thereof, for instance those sold under the name Reflecks by the company Engelhard or those sold under the name Metashine MC 2080GP by the company Nippon Sheet Glass.

These metal-coated glass particles may be coated with silica, for instance those sold under the name Metashine series PSS1 or GPS1 by the company Nippon Sheet Glass.

Particles comprising a spherical glass substrate optionally coated with a metal, especially those sold under the name Prizmalite Microsphere by the company Prizmalite Industries.

Pigments of the Metashine 1080R range sold by the company Nippon Sheet Glass Co. Ltd are also suitable for the invention. These pigments, more particularly described in patent application JP 2001-11340, are C-Glass glass flakes comprising 65% to 72% $SiO_2$, coated with a layer of titanium oxide of rutile type ($TiO_2$). These glass flakes have a mean thickness of 1 micron and a mean size of 80 microns, i.e. a mean size/mean thickness ratio of 80. They have blue, green or yellow tints or a silver shade depending on the thickness of the $TiO_2$ layer.

Particles comprising a silver-coated borosilicate substrate, also known as "white nacres".

Particles comprising a metal substrate such as aluminium, copper or bronze, in the form of platelets, are sold under the trade name Starbrite by the company Silberline and under the name Visionaire by the company Eckart.

Particles comprising a synthetic mica substrate coated with titanium dioxide, and for example particles with a size of between 80 and 100 µm, comprising a synthetic mica (fluorophlogopite) substrate coated with titanium dioxide representing 12% of the total weight of the particle, sold under the name Prominence by the company Nihon Koken.

The particles with a metallic tint may also be chosen from particles formed from a stack of at least two layers with different refractive indices. These layers may be of polymeric or metallic nature and may especially include at least one polymer layer.

Thus, the particles with a metallic effect may be particles derived from a multilayer polymer film.

The choice of materials intended to constitute the various layers of the multilayer structure is obviously made so as to give the particles thus formed the desired metallic effect.

Such particles are especially described in WO 99/36477, U.S. Pat. No. 6,299,979 and U.S. Pat. No. 6,387,498 and more particularly identified below in the goniochromatic section.

Advantageously, the particles with a metallic tint in accordance with the invention are particles with a spherical or non-spherical glass substrate, and also particles with a metallic substrate.

Additives

A composition of the invention may also comprise any additive usually used in the field under consideration, chosen, for example, from surfactants and co-surfactants, polyols, especially of $C_2$-$C_{32}$, pasty compounds, gums, plasticizers, gelling agents, thickeners, antioxidants, dyes, emollients, moisturizers, trace elements, vitamins, preserving agents, fragrances and anti-ageing active agents, and mixtures thereof.

It is a matter of routine operations for a person skilled in the art to adjust the nature and amount of the additives present in the compositions in accordance with the invention such that the desired cosmetic properties thereof are not thereby affected.

Such compositions are especially prepared according to the general knowledge of a person skilled in the art.

Throughout the description, including the claims, the term "comprising a" should be understood as being synonymous with "comprising at least one", unless otherwise mentioned.

The terms "between . . . and . . . " and "ranging from . . . to . . . " should be understood as being inclusive of the limits, unless otherwise specified.

The examples that follow are presented as non-limiting illustrations of the invention. Unless otherwise mentioned, the amounts indicated are expressed as mass percentages.

EXAMPLES

Example 1

Pore-Smoothing Base

| STARTING MATERIAL | Weight % |
|---|---|
| Polyethylene[1] | 6.00 |
| Styrene/methylstyrene/indene copolymer[2] | 4.00 |
| Dimethicone (5 cSt) | 15.00 |
| Dimethicone (2 cSt) | 41.80 |
| Isononyl isononanoate | 5.00 |
| Crosslinked dimethicone/vinyl dimethicone (and) dimethicone polymer[3] | 15.00 |
| Silica silylate[4] | 0.20 |
| Silica/titanium oxide[5] | 8.00 |
| Crosslinked dimethicone/vinyl dimethicone (and) dimethicone polymer[6] | 5.00 |

[1] Performalene 400 polyethylene from New Phase Technologies
[2] Regalite R1100 from Eastman Chemical
[3] KSG-6 from Shin-Etsu
[4] VM-2270 Aerogel Fine Particles from Dow Corning
[5] Sunsil TIN 50 from Sunjin
[6] Dow Corning 9506 Powder from Dow Corning The compounds described above are mixed together and heated to 90° C.

The mixture thus formed is then poured into glass jars. At room temperature, the composition thus obtained has a solid texture with a hardness of 860 g (measured using a P0.5R spindle).

It is easy to manipulate, easy to apply to the face and gives very good smoothing of the pores. Good remanence of this effect over time, i.e. over a period of about 8 hours, is also observed.

The same formulation without the hollow aerogel particles leads to a very greasy feel and to less efficient smoothing of the pores.

Example 2

Smoothing Base

| STARTING MATERIAL | Weight % |
|---|---|
| Polyethylene[1] | 6.00 |
| Trimethyl siloxysilicate[2] | 5.00 |
| Dimethicone (5 cSt) | 15.00 |
| Dimethicone (2 cSt) | 38.70 |
| Dimethicone (100 cSt) | 5.00 |
| Crosslinked dimethicone/vinyl dimethicone (and) dimethicone polymer[3] | 15.00 |
| Silica silylate[4] | 0.30 |
| Silica/titanium oxide[5] | 10.00 |
| Crosslinked dimethicone/vinyl dimethicone polymer[6] | 5.00 |

[1] Performalene 400 polyethylene from New Phase Technologies
[2] SR1000 from Momentive Performance Materials
[3] KSG-6 from Shin-Etsu
[4] VM-2270 Aerogel Fine Particles from Dow Corning
[5] Sunsil TIN 50 from Sunjin
[6] Dow Corning 9506 Powder from Dow Corning The compounds described above are mixed together and heated to 90° C.

This mixture is then cooled through a Clextral BC21 extruder.

At room temperature, the composition thus obtained has a pasty texture with a hardness of 100 g (measured using a P0.5R spindle).

The same composition heated to 70° C. and then poured into glass jars has a hardness of 360 g (measured with a P0.5R spindle).

It is easy to manipulate, easy to apply to the face and gives very good smoothing of the pores. Good remanence of this effect over time, i.e. over a period of about 8 hours, is also observed.

The same formulation without the hollow aerogel particles leads to a very greasy feel and to less efficient smoothing of the pores.

The invention claimed is:

1. A solid anhydrous cosmetic composition, comprising:
   at least 0.1% by weight of hollow particles relative to the total weight of the composition, the hollow particles being hydrophobic silica aerogel particles;
   a volatile oil;
   at least 5% by weight of at least one organopolysiloxane elastomer; and
   a wax which is solid at room temperature,
   wherein the composition has a hardness of greater than or equal to 100 g, and
   the hydrophobic silica aerogel hollow particles have a specific surface area per unit of mass ($S_M$) ranging from 500 to 1500 $m^2/g$ and a size, expressed as the mean volume diameter (D[0.5]), ranging from 1 to 1500 μm.

2. The composition of claim 1, wherein the composition comprises from 0.1% to 5% by weight, of hollow particles relative to the total weight of the composition.

3. The composition of claim 1, wherein the hydrophobic silica aerogel particles have a specific surface area per unit of mass ($S_M$) ranging from 600 to 800 $m^2/g$ and a size expressed as the mean volume diameter (D[0.5]) ranging from 5 to 20 μm.

4. The composition of claim 1, wherein the hydrophobic silica aerogel particles have a tamped density (p) ranging from 0.04 $g/cm^3$ to 0.10 $g/cm^3$.

5. The composition of claim 1, wherein the hydrophobic silica aerogel particles have an oil-absorbing capacity, measured at the wet point, ranging from 5 to 18 ml/g.

6. The composition of claim 1, wherein the hydrophobic silica aerogel particles are trimethylsiloxyl silica particles.

7. The composition of claim 1, wherein the volatile oil is chosen from volatile silicones.

8. The composition of claim 1, wherein the composition comprises from 10% to 60% by weight of the volatile oil relative to the total weight of the composition.

9. The composition of claim 1, wherein the composition comprises from 5% to 50% by weight of the organopolysiloxane elastomer relative to the total weight of the composition.

10. The composition of claim 1, wherein the composition comprises from 1% to 15% by weight of the wax relative to the total weight of the composition.

11. The composition of claim 1, wherein the composition also comprises a hydrophobic film-forming polymer and/or tackifying resin.

12. The composition of claim 11, wherein the composition comprises from 1% to 25% by weight of the hydrophobic film-forming polymer and/or tackifying resin relative to the total weight of the composition.

13. The composition of claim 1, wherein the composition comprises, as a pulverulent phase, besides the hollow particles, at least one particulate material selected from the group consisting of:
- fillers;
- pigments;
- nacres;
- particles with a metallic tint; and
- mixtures thereof.

14. The composition of claim 13, wherein the composition comprises from 1% to 25% by weight of the pulverulent phase relative to the total weight of the composition.

15. A cosmetic process for making up and/or caring for a keratin material, the process comprising applying the composition of claim 1 to the keratin material.

16. A cosmetic process for masking skin relief imperfections, the process comprising applying the composition of claim 1 to a keratin material.

* * * * *